United States Patent [19]

Aguettant et al.

[11] B 4,010,786
[45] Mar. 8, 1977

[54] SEALED CONTAINER

[76] Inventors: Georges Aguettant, l'avenue Jules Carteret; Louis Doyen, 79, rue de Bourgogne, both of Lyon, France

[22] Filed: Apr. 8, 1974

[21] Appl. No.: 459,190

[44] Published under the second Trial Voluntary Protest Program on March 30, 1976 as document No. B 459,190.

[30] Foreign Application Priority Data

Apr. 10, 1973 France .......................... 73.13609

[52] U.S. Cl. .................. 150/8; 141/313; 222/80
[51] Int. Cl.² ...................................... B65D 33/36
[58] Field of Search .............. 206/498; 222/80, 81, 222/89, 91; 150/8; 141/313, 329

[56] References Cited
UNITED STATES PATENTS

| | | | |
|---|---|---|---|
| 3,173,579 | 3/1965 | Curie | 150/8 UX |
| 3,209,752 | 10/1965 | Bujan | 150/8 X |
| 3,255,923 | 6/1966 | Soto | 222/80 |
| 3,340,671 | 9/1967 | Loo | 141/329 X |

FOREIGN PATENTS OR APPLICATIONS 1,298,941   6/1962   France .......................... 150/8

*Primary Examiner*—Donald F. Norton
*Attorney, Agent, or Firm*—Karl F. Ross; Herbert Dubno

[57] ABSTRACT

A container of heat-sealable plastic material, such as PVC, is made by folding a sheet of that material into V-shape and doubling back the vertex of the "V" to form a W-shaped profile, the infolded section or gore of the "W" being sealed except at one or two locations where rigid guide sleeves are inserted and are tightly gripped by the surrounding sheet portions. Each guide sleeve accommodates a hollow plunger for the withdrawal or introduction of fluids, the plunger having a pointed tip designed to pierce the container wall at the ridge of the gore defining the central peak of the W. A resilient annular lip at the outwardly projecting sleeve extremity coacts with two sawtooth-profiled annular grooves on the plunger to index the latter inextractably in a withdrawn position before the piercing step and thereafter in an advanced position so as to prevent leakage. A machine for making a series of such containers from a plastic strip by edge-sealing and transverse cutting includes a pair of sealing dies with semicylindrical recesses and means for feeding successive guide sleeves into pouches formed by these recesses between confronting sheet edges.

6 Claims, 8 Drawing Figures

SEALED CONTAINER

FIELD OF THE INVENTION

Our present invention relates to a container of sealable sheet material, more particularly a thermoplastic resin (e.g. plasticized polyvinylchloride), to be used for the storage and dispensing of a flowable mass such as a liquid or a paste.

BACKGROUND OF THE INVENTION

Containers of the character referred to, which are shatterproof and of light weight, are highly useful for the storage of substances such as medications under sterile conditions. However, once the container wall is ruptured to permit a partial extraction of its contents, e.g. for administration to a patient via a syringe, such sterility is difficult to maintain.

OBJECTS OF THE INVENTION

The object of our present invention, therefore, is to provide means in a container of this nature enabling the partial removal of its contents, and/or the introduction of substances into same, under sterile conditions and with no risk of subsequent contamination.

SUMMARY OF THE INVENTION

A container embodying our invention comprises, essentially, two integrally interconnected and coextensive rectangular portions of sealable sheet material, such as PVC, which are marginally sealed to each other along first, second and third edges and are infolded along the fourth edge, with a W-profile, so as to form an inwardly projecting gore which is spaced from the opposite second edge. The flanks of this gore are sealed to each other and preferably also to overlying outer sheet sections, over part of the length of the fourth edge, while leaving free at least one pouch which is closed by the ridge of the gore against the interior of the container body. A rigid sleeve inserted into that pouch, in fluidtight peripheral contact with the surrounding sheet material, serves as a guide for a sheet-piercing implement slidably lodged therein, this implement having a tubular stem with a pointed tip confronting the gore ridge, initially without piercing that ridge. Advantageously, pursuant to a further feature of our invention, the sleeve and the stem are provided with coacting detent means for preventing extraction of the implement from the sleeve.

Thus, upon an advance of the implement from a withdrawn position into a position of penetration, the tubular stem communicates with the interior of the container body to facilitate either the admission or the withdrawal of flowable material. The aforementioned detent means may be so designed, according to another feature of the invention, as to index the stem in either its initial withdrawn position or its advanced penetrating position without possibility of outward dislodgment, thereby insuring fluidtight contact at all times between the stem and the pouch. Any leakage of the contents from the container by way of the pouch is thereby positively prevented.

The insertion of the guide sleeve into the pouch can be carried out concurrently with the bonding of the gore flanks to each other and to the overlying sheet portions. For this purpose the infolded sheet edge is clamped between two confronting heated dies with registering semicylindrical recesses defining the area of the pouch, the rigid sleeve being positioned between these recesses while the dies are moved toward each other for heat-sealing the four superposed plies to one another around the inserted sleeve.

In the formation of the pouch by a pair of recessed dies or clamp jaws as described above, the sheet portions defining the gore flanks are subjected to a certain tension which stretches them taut around the sleeve shank, provided the sheet material has a certain inherent elasticity.

BRIEF DESCRIPTION OF THE DRAWING

The above and other features of our invention will now be described in detail with reference to the accompanying drawing in which.

SPECIFIC DESCRIPTION

Figure 1:
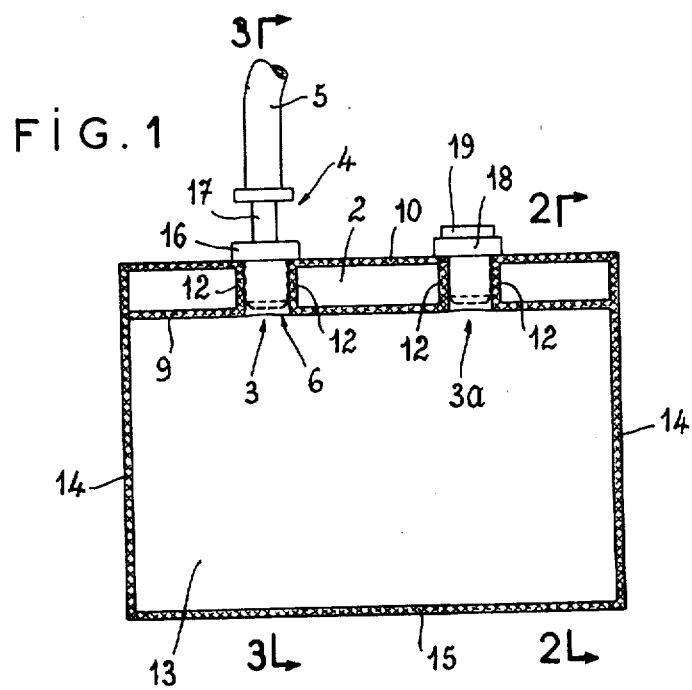
FIG. 1 is a longitudinal sectional view of a container embodying our invention.
Figure 2:
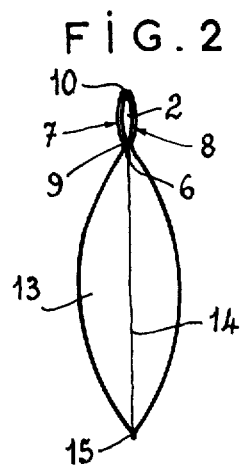
FIGS. 2 and 3 are cross-sectional views respectively taken on the lines 2—2 and 3—3 of FIG. 1.

In FIGS. 1–5 we have shown a container according to our invention made from a sheet 20 (FIGS. 6 and 7) of heat-sealable, flexible thermoplastic material, such as plasticized polyvinylchloride, which could be laminated from two or more layers though this has not been illustrated. The selected sheet material, of course, is to be compatible with the contents to be stored.

Two coextensive sheet halves 13 form a pair of container walls which are marginally bonded to each other along lateral edges 14 and also along a bottom edge 15. The top edge of the container, as viewed in these Figures, is constituted by a pleated section of undulating profile (see FIG. 7) having the cross-section of a W; the infolded part of this profile constitutes a gore with a ridge 6 pointing toward the opposite edge 15. The flanks of the gore define a pocket 2 divided by transverse seams 12 into several rectangular areas closed by longitudinal seams 9 and 10 against the interior of the container body and against the outside. These closed areas have only a sealing function and could therefore also be made completely solid, with the gore flanks and the overlying sheet portions 7 and 8 bonded to each other over the entire area rather than along a rectangular outline as shown. Between these areas there are left two pouches 3 and 3a which initially, as shown in FIGS. 1–4, are sealed by the ridge 6 so as to be separated from the interior of the container body.

A rigid, preferably metallic sleeve 16 is seated in pouch 3. The sleeve comprises a tubular shank 16a, snugly embraced by the pouch walls in fluidtight contact therewith, and a flange 16b secured to that shank preferably by ultrasonic welding. Sleeve 16 forms a guide member for an implememnt 17 in the form of a plunger which is part of a coupling 4 designed to facilitate the extraction of some of the contents stored in the container via a tube 5 which may lead to a transfusion needle. A generally similar sleeve 18 is fitted in like manner into the pouch 3a and is normally closed by a plug 19 made preferably of rubber; with plug 19 removed, sleeve 18 may serve for the guidance of an injection needle designed to introduce additional substance into the container. Upon the first injection, the needle pierces the previously continuous ridge 6 at pouch 3a; in this case, too, the contact between the sleeve and the piercing implement guided thereby should be fluidtight to prevent contamination of the stored substance by contact with the atmosphere.

Figure 3:
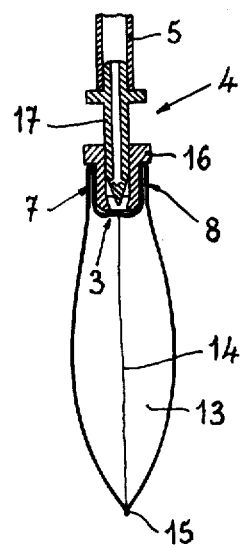
Figure 4:
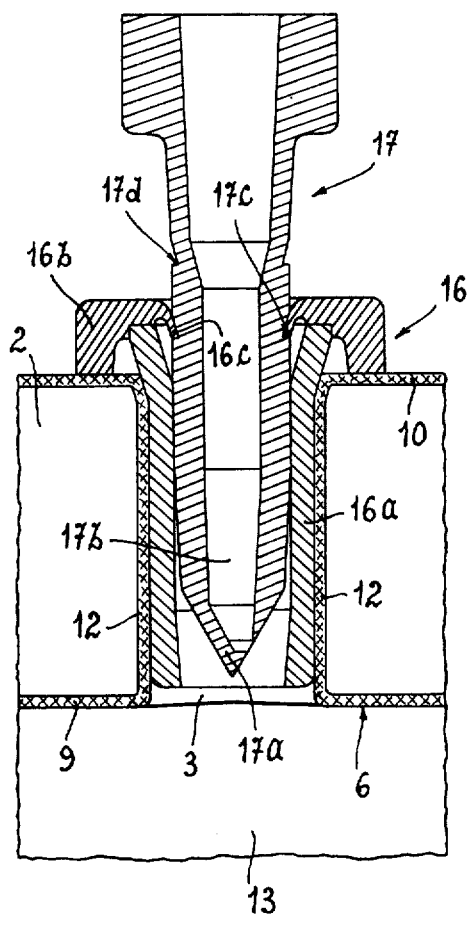
FIGS. 4 and 5 are fragmentary sectional views, similar to FIG. 1 but drawn to a larger scale, of parts of the container provided with external connections.
Figure 5:
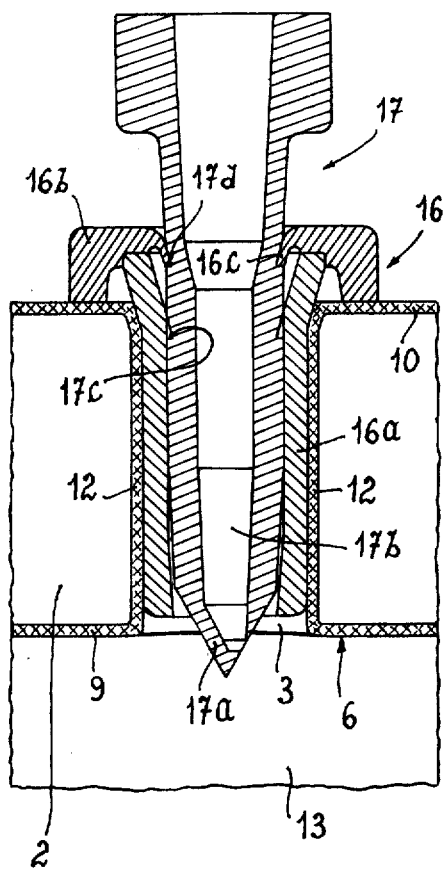

The plunger 17 comprises a tubular stem terminating in a point 17a near a port giving access to its central passage 17b. The stem is formed with a pair of axially spaced annular grooves 17c, 17d of sawtooth profile alternately coacting with a resilient annular lip 16c on flange 16b of sleeve 16. Initially, as shown in FIGS. 1, 3 and 4, the plunger 17 is in a withdrawn position in which its point 17a is spaced from the ridge 6. In this position, lip 16c engages in groove 17c to prevent any upward extraction of the plunger stem from the pouch 3; this engagement also indexes the implement against accidental dislodgement in a downward direction. When it is desired to pierce the ridge 6 for the purpose of withdrawing some material from the container, the implement is advanced into the penetration position shown in FIG. 5 in which the lip 16c engages in the groove 17d. Again, the plunger 17 is backstopped so as to be nonretractably held in sleeve 16.

Figure 6:
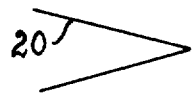
FIGS. 6 and 7 are diagrammatic cross-sectional views illustrating successive steps in the formation of the container.
Figure 7:
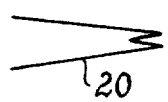
Figure 8:
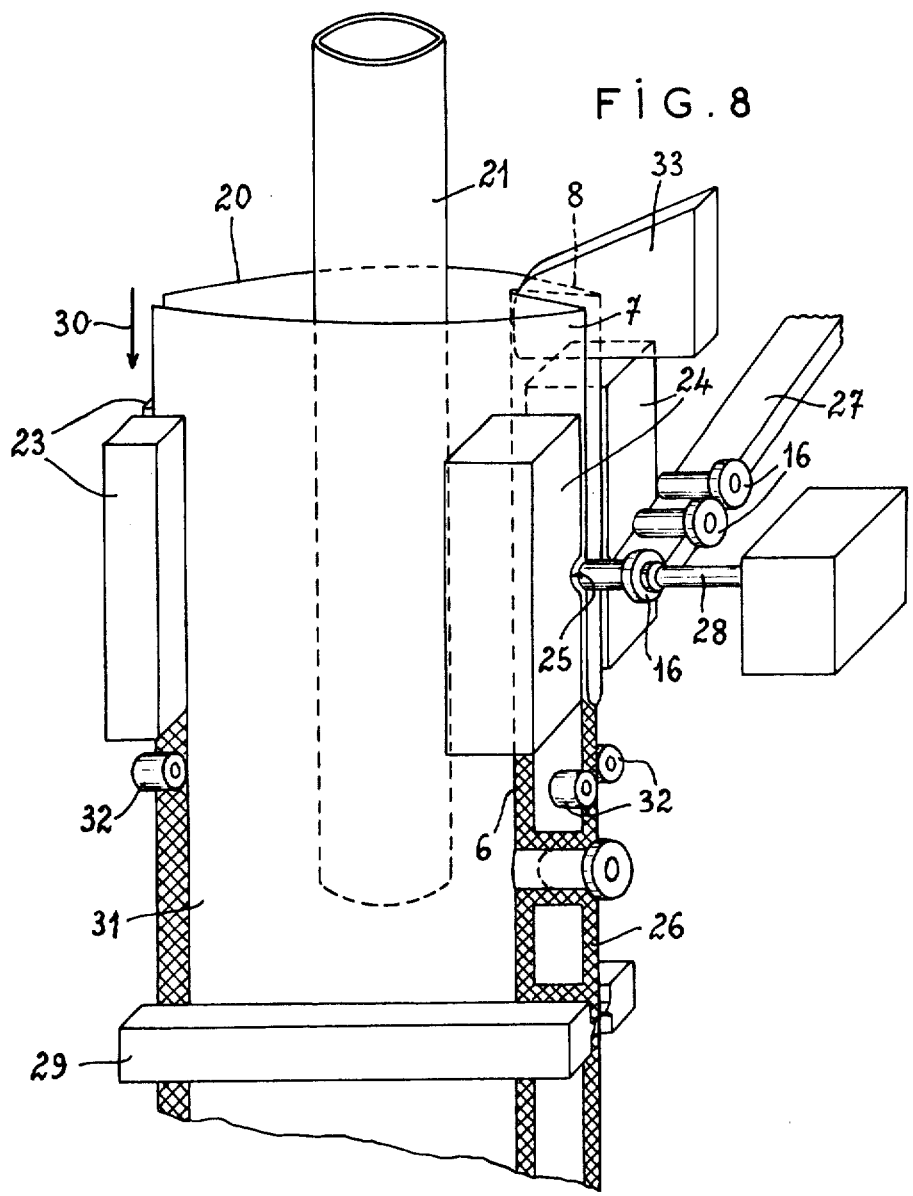
FIG. 8 is a somewhat schematic perspective view of an apparatus for making the container.

Reference will now be made to FIGS. 6–8 for a description of the serial manufacture of such containers from a sheet 20 with simultaneous emplacement of sleeves 16 and/or 18 in the pouches thereof. The sheet 20, which has the shape of an enlongated strip, is first folded about a median line into a V-profile (FIG. 6) and is then infolded at the vertex of the V (FIG. 7) to form the W-profile. This infolding is accomplished with the aid of a stationary deflector 33 past which the sheet 20 is continuously moved in a downward direction (arrow 30) by means of transport rollers 32. The descending, folded strip passes between two pairs of heated dies 23 and 24 which are intermittently movable toward each other to clamp the longitudinal sheet edges between them with formation of marginal bonds, the dies 23 producing the edge seal 15 (FIGS. 1-3) whereas the dies 24 provide rectangular seams 26 between outer sheet portions 7, 8 and the adjoining gore flanks. Two further dies 29, extending transversely across the strip path, are provided with longitudinal cutting edges, whereby the strip is severed into sections 31 each bounded by a seam 14 (cf. FIGS. 1-3), the cutting edge passing midway through the heat seal produced by the dies 29. A filling tube 21, about whose lower end the oncoming strip is being continuously folded, extends into the space between the sheet halves to introduce a fluid substance into each upwardly open section 31 just prior to its closure by the operation of the transverse dies 29.

The lateral dies 24 are provided with confronting semicylindrical recesses 25 of a radius slightly larger than that of sleeves 26 which are fed into alignment with these recesses via a chute 27. A push rod 28 is periodically actuated by a mechanism 22, synchronized with the transport rollers 32 and the hydraulic or other die-operating means (not shown), so as to insert a fresh sleeve 16 into the gore of the strip between the recesses 25 of the separated dies 24. Upon the subsequent closure of the dies, the sleeve 16 is firmly embraced by the sheet material whose four superposed plies are simultaneously bonded to one another along zones 26 on opposite sides of the sleeve.

The sealing of the opposite strip edge by the dies 23 may take place simultaneously with the operation of dies 24 or in staggered relationship therewith.

The advance of the strip by the transport rollers 32 is preferably intermittent, being halted during closure of the dies and severance of a section 31. The completed and filled container constituted by such a section may be sterilized and wrapped if required.

Thus, it will be seen that we have provided an efficient method of and apparatus for making sterile containers which can be used, for example, for the storage of whole blood or other physiological solutions to be transfused into the veins of a patient.

We claim:

1. A container comprising a hollow body of sealable sheet material with two integrally interconnected and coextensive rectangular portions marginally sealed to each other along first, second and third edges and infolded along the fourth edge to form an inwardly projecting gore with a ridge spaced from said second edge opposite said fourth edge, the flanks of said gore being sealed to each other over part of the length of said fourth edge with formation of at least one outwardly open pouch closed by said ridge and separated thereby from the interior of said body, and a rigid sleeve inserted into said pouch in fluidtight peripheral contact with the surrounding sheet material of said gore.

2. A container as defined in claim 1, further comprising a sheet-piercing implement slidably lodged in said sleeve, said implement having a tubular stem adapted to be joined to an external conduit, said stem having a pointed tip confronting said ridge.

3. A container as defined in claim 2 wherein said sleeve and said stem are provided with coacting detent means for preventing extraction of said implement from said sleeve.

4. A container as defined in claim 3 wherein said detent means comprises a first formation on said sleeve and coacting second formations on said stem for successively indexing said stem in a withdrawn position and in an advanced position, said tip being spaced from said ridge in said withdrawn position but penetrating said ridge in said advanced position, said sleeve and said stem engaging each other in a fluidtight manner for preventing leakage of the contents of said body in said advanced position.

5. A container as defined in claim 4 wherein said first formation is a resilient annular lip and said second formations are a pair of parallel annular grooves of sawtooth profile.

6. A container as defined in claim 1 wherein said flanks are bonded to overlying outer sheet sections of said rectangular portions along said first and third edges and at the lateral boundaries of said pouch.

* * * * *